(12) United States Patent
Herweck et al.

(10) Patent No.: US 6,395,208 B1
(45) Date of Patent: *May 28, 2002

(54) METHOD OF MAKING AN EXPANDABLE FLUOROPOLYMER DEVICE

(75) Inventors: Steve A. Herweck, Nashua; Peter H. Gingras, Windham; Paul Martakos, Pelham; Theodore Karwoski, Hollis, all of NH (US)

(73) Assignee: Atrium Medical Corporation, Hudson, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/410,329

(22) Filed: Oct. 1, 1999

Related U.S. Application Data

(60) Provisional application No. 60/117,152, filed on Jan. 25, 1999.

(51) Int. Cl.[7] .......................... B29C 49/04; B29C 49/10; B29C 51/04; B29C 55/24; B29C 55/26
(52) U.S. Cl. ................. 264/127; 264/532; 264/573; 264/209.5; 264/210.7; 264/210.2; 264/235.6; 264/288.8; 264/296; 264/314; 264/346; 604/96
(58) Field of Search ................................ 264/127, 532, 264/573, 209.5, 210.7, 210.2, 235, 235.6, 288.8, 296, 314, 346; 604/96

(56) References Cited

U.S. PATENT DOCUMENTS

| | | | |
|---|---|---|---|
| 3,635,223 A | 1/1972 | Klieman | 128/348 |
| 3,888,249 A | 6/1975 | Spencer | 128/214 |
| 3,901,232 A | 8/1975 | Michaels et al. | 128/260 |
| 3,981,299 A | 9/1976 | Murray | 128/349 |
| 4,030,503 A | 6/1977 | Clark, III | 128/304 |

(List continued on next page.)

FOREIGN PATENT DOCUMENTS

| | | |
|---|---|---|
| EP | 293090 A2 | 11/1988 |
| EP | 383429 A2 | 8/1990 |
| EP | 531117 A2 | 3/1993 |
| EP | 788774 A1 | 8/1997 |

(List continued on next page.)

OTHER PUBLICATIONS

Lambert, C.R. et al., "Local drug delivery catheters; functional comparison of porous and microporous designs," *Current Science*, 4(5):469–475 (1993).

Wolinsky, H., "Historical perspective," *Semin Intervent Cardiol* 1:3–7 (1996).

*Primary Examiner*—Jan H. Silbaugh
*Assistant Examiner*—Michael I. Poe
(74) *Attorney, Agent, or Firm*—Lahive & Cockfield, LLP

(57) ABSTRACT

A method of making a radially expandable device having a body constructed of a generally inelastic, expanded fluoropolymer material. The body is deployable upon application of a radial expansion force from a reduced diameter, collapsed configuration to an expanded configuration having a pre-defined and fixed increased diameter. The body has a singular, unitary construction of generally homogenous material that is characterized by a seamless construction of expanded fluoropolymer material, such as expanded polytetrafluoroethylene (ePTFE), and is preferably constructed through an extrusion and expansion process. The body is further characterized by a microstructure of nodes interconnected by fibrils in which substantially all the nodes of the body are oriented generally perpendicularly to the longitudinal axis of the body. The monolithic construction of the body and the orientation of the nodes, perpendicular to the longitudinal axis of the body, yields a radially expandable device that predictably and dependably expands to a predefined, fixed maximum diameter that is generally independent of the expansion force used to radially expand the device.

26 Claims, 6 Drawing Sheets

U.S. PATENT DOCUMENTS

| | | | |
|---|---|---|---|
| 4,229,838 A | | 10/1980 | Mano .............................. 3/1.4 |
| 4,327,721 A | | 5/1982 | Goldin et al. .......... 128/207.15 |
| 4,338,942 A | | 7/1982 | Fogarty ...................... 128/344 |
| 4,406,656 A | | 9/1983 | Hattler et al. ............... 604/280 |
| 4,417,576 A | | 11/1983 | Baran .................... 128/207.15 |
| 4,423,725 A | | 1/1984 | Baran et al. ........... 128/207.15 |
| 4,437,856 A | | 3/1984 | Valli ............................ 604/29 |
| 4,490,421 A | * | 12/1984 | Levy ............................ 428/35 |
| 4,573,966 A | | 3/1986 | Weikl et al. .................. 604/53 |
| 4,636,195 A | | 1/1987 | Wolinsky ..................... 604/53 |
| 4,637,396 A | | 1/1987 | Cook ......................... 128/344 |
| 4,650,466 A | | 3/1987 | Luther .......................... 604/95 |
| 4,692,200 A | | 9/1987 | Powell ....................... 156/289 |
| 4,693,243 A | | 9/1987 | Buras .................... 128/207.15 |
| 4,711,251 A | | 12/1987 | Stokes ....................... 128/784 |
| 4,713,070 A | | 12/1987 | Mano ............................ 623/1 |
| 4,714,460 A | | 12/1987 | Calderon ..................... 604/28 |
| 4,714,461 A | | 12/1987 | Gabel .......................... 604/53 |
| 4,721,507 A | | 1/1988 | Chin .......................... 604/100 |
| 4,744,366 A | | 5/1988 | Jang ........................... 128/344 |
| 4,762,130 A | | 8/1988 | Fogarty et al. .......... 128/348.1 |
| 4,799,479 A | | 1/1989 | Spears ..................... 128/303.1 |
| 4,820,349 A | | 4/1989 | Saab ........................... 128/344 |
| 4,824,436 A | | 4/1989 | Wolinsky ..................... 604/53 |
| 4,832,688 A | | 5/1989 | Sagae et al. ................... 64/53 |
| RE32,983 E | * | 7/1989 | Levy ....................... 428/36.92 |
| 4,850,969 A | | 7/1989 | Jackson ........................ 604/96 |
| 4,877,031 A | | 10/1989 | Conway et al. ............. 128/344 |
| 4,935,190 A | * | 6/1990 | Tennerstedt ................. 264/529 |
| 4,957,669 A | * | 9/1990 | Primm ......................... 264/23 |
| 4,968,306 A | | 11/1990 | Huss et al. ................. 604/264 |
| 4,968,307 A | | 11/1990 | Dake et al. ................. 604/264 |
| 4,994,033 A | | 2/1991 | Shockey et al. ............ 604/101 |
| 5,015,232 A | | 5/1991 | Maglinte ...................... 604/96 |
| 5,021,044 A | | 6/1991 | Sharkawy ..................... 604/53 |
| 5,034,082 A | * | 7/1991 | Nolan ......................... 156/245 |
| 5,041,090 A | | 8/1991 | Scheglov et al. ........... 604/101 |
| 5,049,132 A | | 9/1991 | Shaffer et al. .............. 604/101 |
| 5,071,424 A | | 12/1991 | Reger ......................... 606/159 |
| 5,087,244 A | | 2/1992 | Wolinsky et al. ............. 604/53 |
| 5,087,247 A | | 2/1992 | Horn et al. .................... 604/98 |
| 5,087,394 A | * | 2/1992 | Keith ......................... 204/22 |
| 5,098,381 A | | 3/1992 | Schneider .................... 604/96 |
| 5,100,383 A | | 3/1992 | Lichtenstein ................. 604/96 |
| 5,112,305 A | | 5/1992 | Barath et al. ................. 604/96 |
| 5,112,347 A | | 5/1992 | Taheri ........................ 606/200 |
| 5,156,610 A | | 10/1992 | Reger ......................... 606/159 |
| 5,176,638 A | | 1/1993 | Don Michael .............. 604/101 |
| 5,192,290 A | | 3/1993 | Hilal ........................... 606/159 |
| 5,199,951 A | | 4/1993 | Spears ......................... 604/96 |
| 5,211,651 A | | 5/1993 | Reger et al. ................. 606/159 |
| 5,213,576 A | | 5/1993 | Abiuso et al. ................ 604/96 |
| 5,232,444 A | | 8/1993 | Pinchuk et al. ............. 264/573 |
| 5,254,089 A | | 10/1993 | Wang .......................... 604/96 |
| 5,269,755 A | | 12/1993 | Bodicky ..................... 604/535 |
| 5,279,565 A | | 1/1994 | Klein et al. ................. 604/105 |
| 5,282,484 A | | 2/1994 | Reger ......................... 128/898 |
| 5,286,254 A | | 2/1994 | Shapland et al. ............. 604/21 |
| 5,295,962 A | | 3/1994 | Crocker et al. ............. 604/101 |
| 5,304,340 A | * | 4/1994 | Downey ..................... 264/521 |
| 5,318,531 A | | 6/1994 | Leone .......................... 604/96 |
| 5,405,472 A | | 4/1995 | Leone ........................ 156/218 |
| 5,433,909 A | | 7/1995 | Martakos et al. ......... 264/209.1 |
| 5,456,661 A | | 10/1995 | Narciso ........................ 604/20 |
| 5,458,568 A | | 10/1995 | Racchini et al. .............. 604/19 |
| 5,474,824 A | | 12/1995 | Martakos et al. .......... 428/36.9 |
| 5,499,995 A | | 3/1996 | Teirstein ..................... 606/192 |
| 5,500,180 A | | 3/1996 | Anderson et al. ........... 264/532 |
| 5,500,181 A | | 3/1996 | Wang et al. ................. 264/532 |
| 5,512,051 A | | 4/1996 | Wang et al. .................. 604/96 |
| 5,514,092 A | | 5/1996 | Forman et al. ............. 604/101 |
| 5,628,730 A | | 5/1997 | Shapland et al. ............. 604/21 |
| 5,709,653 A | | 1/1998 | Leone .......................... 604/20 |
| 5,713,853 A | | 2/1998 | Clark et al. ................... 604/53 |
| 5,752,934 A | | 5/1998 | Campbell et al. ............. 604/96 |
| 5,772,632 A | | 6/1998 | Forman ...................... 604/101 |
| 5,782,797 A | | 7/1998 | Schweich, Jr. et al. ....... 604/49 |
| 5,810,767 A | | 9/1998 | Klein ........................... 604/53 |
| 5,823,996 A | | 10/1998 | Sparks ......................... 604/96 |
| 5,843,033 A | | 12/1998 | Ropiak ........................ 604/96 |
| 5,860,954 A | | 1/1999 | Ropiak ........................ 604/96 |
| 5,868,704 A | | 2/1999 | Campbell et al. ............. 604/96 |
| 5,868,719 A | | 2/1999 | Tsukernik ................... 604/265 |
| 5,902,266 A | | 5/1999 | Leone et al. .................. 604/53 |
| 5,948,345 A | * | 9/1999 | Patel et al. .................. 264/529 |
| 6,120,477 A | | 9/2000 | Campbell et al. ............. 604/96 |

FOREIGN PATENT DOCUMENTS

| | | |
|---|---|---|
| EP | 835673 A2 | 4/1998 |
| JP | 5-305146 * | 11/1993 .......... A61M/25/00 |
| WO | WO 87/06846 | 11/1987 |
| WO | WO 89/12478 | 12/1989 |
| WO | WO 91/08790 | 6/1991 |
| WO | WO 97/10871 | 3/1997 |
| WO | WO 97/17889 | 5/1997 |
| WO | WO 97/31590 | 9/1997 |
| WO | WO 98/26731 | 6/1998 |
| WO | WO 98/31415 | 7/1998 |
| WO | WO 98/33638 | 8/1998 |
| WO | WO 99/16500 | 4/1999 |

* cited by examiner

METHOD OF MAKING AN EXPANDABLE FLUOROPOLYMER DEVICE

REFERENCE TO RELATED APPLICATIONS

This application claims priority to Provisional Application Ser. No. 60/117,152, filed Jan. 25, 1999, and incorporated herein by reference.

BACKGROUND OF THE INVENTION

Radially expandable devices are utilized in a wide range of applications including a number of biological applications. Radially expandable devices in the form of inflatable balloons have been proposed for treatment of body passages occluded by disease and for maintenance of the proper position of catheter delivered medical devices within such body passages. Such expandable devices can be constructed of elastomeric materials such as latex. A number of general problems are associated with such elastomeric balloons. Balloons and other expansion devices constructed of elastomeric materials can lack a maximum inflation or expansion diameter in that the prolonged application of an inflation medium will cause the balloon to continuously expand until the balloon bursts. Thus, over inflation of an elastomeric balloon may result in damage to the body vessel or organ being treated or may result in the balloon bursting within the body. Elastomeric balloons frequently do not inflate symmetrically and may not inflate to the desired size and shape. Asymmetrical expansion, as well as failure of the balloon to properly inflate, can lead to incomplete treatment of the body vessel. The high coefficient of friction of most elastomeric materials, such as latex, can result in damage to one or more cellular layers of the wall of the body vessel or organ being treated. Additionally, elastomeric expansion devices generally have insufficient strength for a number of applications, such as compressing deposits formed on vascular walls and positioning catheter delivered medical devices.

SUMMARY OF THE INVENTION

The present invention provides a radially expandable device having a body constructed a fluoropolymer material, such as expanded polytetrafluoroethylene (ePTFE). The use of fluoropolymer materials provides a radial expandable device having a biocompatible and inelastic construction that is suitable for numerous uses including the treatment of body vessels, organs, and implanted grafts. The body of the radially expandable device has a longitudinal axis and a wall having a thickness transverse to the longitudinal axis. The wall of the body is characterized by a microstructure of nodes interconnected by fibrils. The body of the radially expandable device is deployable from a reduced diameter, collapsed configuration to an increased diameter, expanded configuration upon application of an expansion force to the radially expandable device. Along at least a portion of the body, substantially all the nodes of the microstructure are oriented generally perpendicularly to the longitudinal axis of the body. This orientation of the nodes, perpendicular to the longitudinal axis of the body, yields a radially expandable device that predictably and dependably expands to the increased diameter configuration.

According to one aspect of the present invention, the body of the radially expandable device has a monolithic construction. The term "monolithic", as used herein, includes structures having a singular, unitary construction of generally homogenous material. The monolithic body of the radially expandable device of the present invention is characterized by a seamless construction of fluoropolymer material, such as expanded polytetrafluoroethylene (ePTFE), preferably constructed through an extrusion and expansion process. Because the cross section of the monolithic body is singular or unitary, the expandable device lacks seams or internal interfaces between adjacent layers that can result in unreliable expansion of the device. The monolithic construction of the body of the present invention contributes to the dependable and predictable expansion of the body to a predefined, fixed maximum diameter that is generally independent of the expansion force used to radially expand the device.

In accordance with a further aspect of the present invention, a method is provided for manufacturing a radially expandable device constructed of a fluoropolymer material such as, for example, ePTFE. The method includes the step of forming a tube of fluoropolymer material having an initial diameter. A radial expansion force is applied to the tube to expand the tube from the initial diameter to a second diameter. The expansion force is then removed. The resultant tube is radially expandable from a reduced diameter to the second diameter upon application of a radial deployment force from a deployment mechanism within the tube. The deployment mechanism can be, for example, a fluid injected into the tube or a radial expansion element inserted into the tube.

A radially expandable device constructed in accordance with the method of the present invention can be dependably and predictably expanded to the second diameter upon the application of a radially deployment force within the tube. The second diameter can be predefined and fixed to a maximum expansion diameter through the manufacturing process of the present invention, resulting in an expansion device having a maximum expansion diameter that is generally independent of the radial deployment force applied to the device.

The fluoropolymer tube can be constructed through an extrusion and expansion process including the step of creating a billet by blending a mixture of a fluoropolymer and a lubricant and compressing the mixture. The fluoropolymer is preferably PTFE. The billet can then be extruded to form an extruded article. The lubricant is removed and the extruded article is expanded to form a monolithic tube of inelastic, expanded fluoropolymer material. The stretched tube is then heat set to lock in the microstructure of the tube and maintain the tube in the stretched state.

The extruded article is preferably bilaterally stretched in two opposing directions along the longitudinal axis of the article. Bilaterally stretching the extruded article yields an article that is substantially uniformly stretched over a major portion of its length and has a microstructure of nodes interconnected by fibrils. The bilateral stretching step can be carried out by displacing the ends of the extruded article either simultaneously or sequentially. The longitudinal stretch ratio of the expanded tube, i.e., the ratio of the final stretched length of the tube to the initial length, and the diametric stretch ratio, i.e., the ratio of the final diameter, after longitudinal stretching, and the initial diameter, can be varied to yield an expansion device having differing radial expansion properties. For example, the magnitude of the deployment force necessary to expand the expansion device of the present invention can be pre-selected and manipulated by varying the stretch ratios of the fluoropolymer tube. Additionally, the stretch rate can be varied to selectively provide the expansion device with improved expansion characteristics.

In accordance with another aspect of the present invention, the step of applying a radial expansion force to the fluoropolymer tube is carried out by inserting a balloon into the tube and expanding the balloon to apply the radial expansion force to the tube. Preferably, the balloon is constructed from an inelastic material such as, for example, polyethylene terephthalate (PET) or nylon. In a preferred embodiment, the balloon is constructed to be expandable to a predefined size and shape by inflation with a fluid. Radial expansion of the fluoropolymer tube with such an inelastic balloon imparts the predetermined size and shape of the balloon to the expanded fluoropolymer balloon.

In accordance with a further aspect of the present invention, the step of radially expanding the fluoropolymer tube plastically deforms the tube beyond its elastic limit to the second diameter. Plastically deforming the fluoropolymer tube to the second diameter contributes to expansion device dependably expanding to the second diameter upon application of the radial deployment force.

The step of radially expanding the fluoropolymer tube can also include the steps of positioning the tube within the internal cavity of a mold fixture and radially expanding the balloon within the tube while the tube remains positioned in the internal mold cavity. The internal mold cavity preferably has a size and shape analogous to the predefined size and shape of the balloon. The internal cavity of the mold facilitates concentric radial expansion of the balloon and the fluoropolymer tube.

In accordance with another aspect of the present invention, the step of applying a radial expansion force to the fluoropolymer tube is carried out by inserting a second tube constructed from an extruded inelastic material, such as extruded PET, into the fluoropolymer tube and expanding the second tube to apply the radial expansion force to the tube. Preferably, the fluoropolymer tube and the second tube are heated to a temperature less than or equal to the glass transition temperature of the extruded material forming the second tube during the radial expansion step. The heating of the tubes can be accomplished by submerging the tubes into a hot water bath. Alternatively, the fluoropolymer tube can be expanded by the second tube within a heated mold.

In accordance with a further aspect of the present invention, the radially expandable device of the present invention is particularly suited for treatment of body passages occluded by disease. The expandable device can be utilized in the manner of a catheter balloon suitable for deployment within a body vessel by a catheter. Exemplary treatment applications of the present application include dilation of stenoic blood vessels in a percutaneous transluminal angioplasty procedure (PTA), removal of thrombi and emboli from obstructed blood vessels, urethra dilation to treat prostatic enlargement due to benign prostate hyperplasia (BPH) or prostatic cancer, and generally restoring patency to implanted grafts or body passages such as blood vessels, the urinary tract, the intestinal tract, the kidney ducts, or other body passages.

BRIEF DESCRIPTION OF THE DRAWINGS

These and other features and advantages of the present invention will be more fully understood by reference to the following detailed description in conjunction with the attached drawings in which like reference numerals refer to like elements through the different views. The drawings illustrate principles of the invention and, although not to scale, show relative dimensions.

DETAILED DESCRIPTION OF THE PREFERRED EMBODIMENTS

Figure 1:
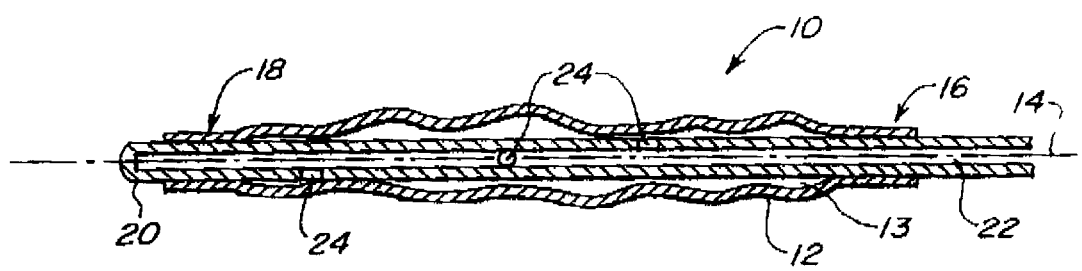
FIG. 1 is a side elevational view in cross-section of a radially expandable device according to the teachings of the present invention, illustrating the device in a first, reduced diameter configuration.
Figure 2:
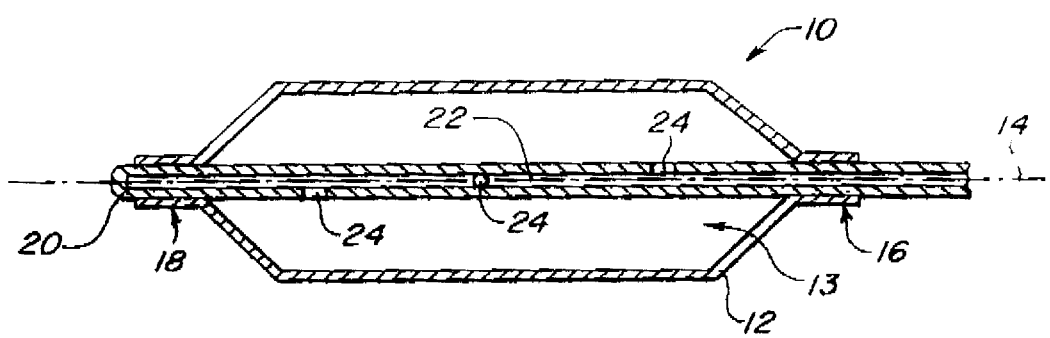
FIG. 2 is a side elevational view in cross-section of the radially expandable device of FIG. 1, illustrating the device in a second, increased diameter configuration.

A radially expandable device 10 having a body 12 constructed of a generally inelastic, expanded fluoropolymer material is illustrated in FIGS. 1 and 2. Expandable devices provided by the present invention are suitable for a wide range of applications including, for example, a range of medical treatment applications. Exemplary biological applications include use as a catheter balloon for treatment of implanted grafts and body passages such as blood vessels, the urinary tract, the intestinal tract, kidney ducts, etc. Specific examples include as a device for the removal of obstructions such as emboli and thrombi from blood vessels, as a dilation device to restore patency to an occluded body passage as an occlusion device to selectively obstruct a body passage, and as a centering mechanism for transluminal instruments and catheters. The expandable device of the present invention can also be used as a sheath for covering conventional catheter balloons to control the expansion of the conventional balloon.

The body 12 of the radially expandable device 10 is deployable upon application of an expansion force from a first, reduced diameter configuration, illustrated in FIG. 1, to a second, increased diameter configuration, illustrated in FIG. 2. The body 12 of the expansion device 10 of the present invention preferably features a monolithic construction, i.e., the body 12 is a singular, unitary article of generally homogeneous material. The body 12 is manufactured in accordance with the methods of manufacturing of the present invention, an extrusion and expansion process described in detail below, to yield a body 12 characterized by a seamless construction of inelastic, expanded fluoropolymer having a predefined size and shape in the second, increased diameter configuration. The body 12 can be dependably and predictably expanded to the predefined, fixed maximum diameter and to the predefined shape independent of the expansion force used to expand the device.

Referring specifically to FIG. 2, the body 12 of the radial expansion device 10 of the present invention is preferably generally tubular in shape when expanded, although other cross sections, such as rectangular, oval, elliptical, or polygonal, can be utilized. The cross section of the body 12 is preferably continuous and uniform along the length of the body. However, in alternative embodiments, the cross section can vary in size and/or shape along the length of the body. FIG. 1 illustrates the body 12 relaxed in the first, reduced diameter configuration. The body 12 has a central lumen 13 extending along a longitudinal axis 14 between a first end 16 and second end 18.

A deployment mechanism in the form of an elongated hollow tube 20 is shown positioned within the central lumen 13 to provide a radial deployment or expansion force to the body 12. The radial deployment force effects radial expansion of the body 12 from the first configuration to the second increased diameter configuration illustrated in FIG. 2. The first end 16 and the second end 18 are connected in sealing relationship to the outer surface of the hollow tube 20. The first and second ends 16 and 18 can be thermally bonded, bonded by means of an adhesive, or attached by other means suitable for inhibiting fluid leakage from the first and second ends 16 and 18 between the walls of the body 12 and the tube 20.

The hollow tube 20 includes an internal, longitudinal extending lumen 22 and a number of side-holes 24 that provide for fluid communication between the exterior of the tube 20 and the lumen 22. The tube 20 can be coupled to a fluid source (not shown) to selectively provide fluid, such as water, saline, or air, to the lumen 13 of the body 12 through the lumen 22 and side-holes 24. The pressure from the fluid provides a radial expansion force on the body 12 to radial expand the body 12 to the second, increased diameter configuration. Because the body 12 is constructed from an inelastic material, uncoupling the tube 20 from the fluid source or otherwise substantially reducing the fluid pressure within the lumen 13 of the body 12, does not generally result in the body 12 returning to the first, reduced diameter configuration. However, the body 12 will collapse under its own weight to a reduced diameter. Application of negative pressure, from, for example, a vacuum source, can be used to completely deflate the body 12 to the initial reduced diameter configuration.

One skilled in the art will appreciate that the expansion device 10 of the present invention is not limited to use with deployment mechanisms employing a fluid deployment force, such as hollow tube 20. Other known deployment mechanisms can be used to radially deploy the expansion device 10 including, for example, mechanical operated expansion elements, such as mechanically activated members or mechanical elements constructed from temperature activated materials such as nitinol.

Various fluoropolymer materials are suitable for use in the present invention. Suitable fluoropolymer materials include, for example, polytetrafluoroethylene (PTFE) or copolymers of tetrafluoroethylene with other monomers may be used. Such monomers include ethylene, chlorotrifluoroethylene, perfluoroalkoxytetrafluoroethylene, or fluorinated propylenes such as hexafluoropropylene. PTFE is the preferred material of choice. Accordingly, while the radial expansion device 10 can be manufactured from various fluoropolymer materials, and the manufacturing methods of the present invention can utilize various fluoropolymer materials, the description set forth herein refers specifically to PTFE.

Figure 4A:
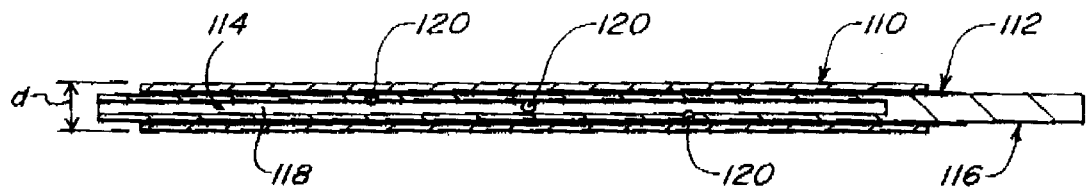
FIG. 4A is a side elevational view in cross-section of an inelastic balloon positioned within an expanded fluoropolymer tube, illustrating the inelastic balloon in a deflated condition in accordance with a method of manufacturing a radially expandable device according to the teachings of the present invention.

A method of manufacturing a radially expandable device in accordance with the present invention will be described in connection with FIGS. 4A–4C and the flow chart shown in FIG. 6A. The radially expandable device 10 of the present invention is produced from a tube 110 constructed of expanded fluoropolymer material, which is preferably produced through an extrusion and a longitudinal expansion process. The preferred fluoropolymer material is expanded PTFE (ePTFE), which is a hydrophobic, biocompatible, inelastic material having a low coefficient of friction, although, as discussed above, other inelastic, biocompatible fluoropolymer materials may be used.

To produce the ePTFE tube, a billet comprising a PTFE resin mixed with an organic lubricant is utilized. Various organic lubricants are suitable such as naphtha, ISOPAR-G and ISOPAR-H (the ISOPAR products being hydrocarbon fluids) available from Exxon Corporation. The blended resin is compressed at low pressure to yield a tubular billet of PTFE resin and lubricant, step 210 of FIG. 6A. The tubular billet is then extruded through an extruder, for example a ram extruder, to reduce the cross section of the billet and to yield a tubular extrudate, step 212. The organic lubricant can be removed from the extrudate by drying the extrudate in a heated oven, step 214.

Once the tubular extrudate is produced, the extrudate is expanded by longitudinal stretching, step 216. Preferably, the extrudate is bilaterally stretched. Bilateral stretching is accomplished by displacing both ends of the extrudate, sequentially or simultaneously, away from the center of the extrudate. Bilateral stretching provides a material that is homogeneously stretched over the majority of its length. After the extrudate has been stretched, it is heat set to lock in the microstructure of the material, step 218 of FIG. 6A, and to complete the process of the forming the tube 110 of ePTFE.

Figure 3:
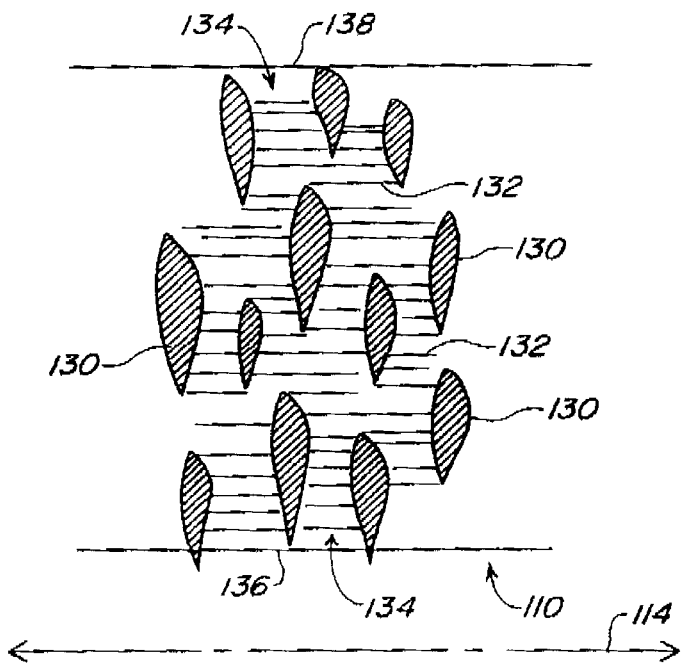
FIG. 3 is a schematic representation of the microstructure of a section of the wall of an expanded fluoropolymer tube used during the manufacturing process of the present invention to yield the radially expandable device of the present invention.

FIG. 3 is a schematic representation of the microstructure of the walls of the ePTFE tube 110 as formed by the extrusion and expansion process described above. For purposes of description, the microstructure of the tube 110 has been exaggerated. Accordingly, while the dimensions of the microstructure are enlarged, the general character of the illustrated microstructure is representative of the microstructure prevailing within the tube 110.

The microstructure of the ePTFE tube 110 is characterized by nodes 130 interconnected by fibrils 132. The nodes 130 are generally oriented perpendicular to the longitudinal axis 114 of the tube 110. This microstructure of nodes 130 interconnected by fibrils 132 provides a microporous structure having microfibrillar spaces which define through-pores or channels 134 extending entirely from the inner wall 136 and the outer wall 138 of the tube 110. The through-pores 134 are perpendicularly oriented (relative to the longitudinal axis 114), internodal spaces that traverse from the inner wall 136 to the outer wall 138. The size and geometry of the through-pores 134 can be altered through the extrusion and stretching process, as described in detail in Applicants'copending U.S. patent application Ser. No. 09/411/797, filed on Oct. 1, 1999 , which is incorporated herein by reference, to yield a mnicrostructure that is impermeable, semi-impermeable, or permeable.

In a preferred embodiment, the ePTFE tube 110, and the resultant expandable device 10, has a fine nodal structure that is uniform throughout the cross section and length of the ePTFE tube. The preferred uniform fine nodal structure provides the expandable device 10 with improved expansion characteristics as the expandable device dependably and predictably expands to the second diameter. The preferred fine nodal structure is characterized by nodes having a size and mass less than the nodes found in conventional ePTFE grafts, preferably in the range of 25 $\mu$m–30 $\mu$m. Additionally, the spacing between the nodes, referred to as the internodal distance, and the spacing between the fibers, referred to as the interfibril distance, is also preferably less than found in conventional ePTFE grafts, preferably in the range of 1 $\mu$m–5 $\mu$m. Moreover, the internodal distance and the interfibril distance in the preferred embodiment is preferably uniform throughout the length and the cross section of the ePTFE tube. The preferred uniform nodal structure can be created by forming the billet with a uniform lubricant level throughout its cross section and length. Stretching the tubular extrudate at higher stretch rates, for example at rates greater than 1 in/s, yields the preferred fine nodal structure. Preferably, the extrudate is stretched at a rate of approximately 10 in/s or greater.

Continuing to describe the manufacturing method of the present invention and referring again to FIGS. 4A and 6A, the ePTFE tube 110, having an initial diameter d, is pulled over a balloon 112 to position the balloon 112 within the lumen 114 of the tube 110, step 220 of FIG. 6A. The balloon 112 is preferably constructed of an inelastic material such as, for example, PET or nylon, such that the balloon 112, when inflated, attains a predetermined size and shape. The balloon 112 can be bonded or otherwise coupled to a rigid catheter or hypo-tube 116 to facilitate placement and removal of the ePTFE tube as described below. The catheter 116 has a central inflation lumen 118 and a plurality of side-holes 120 to provide for the delivery of an inflation fluid to inflate the balloon 112.

Figure 4B:
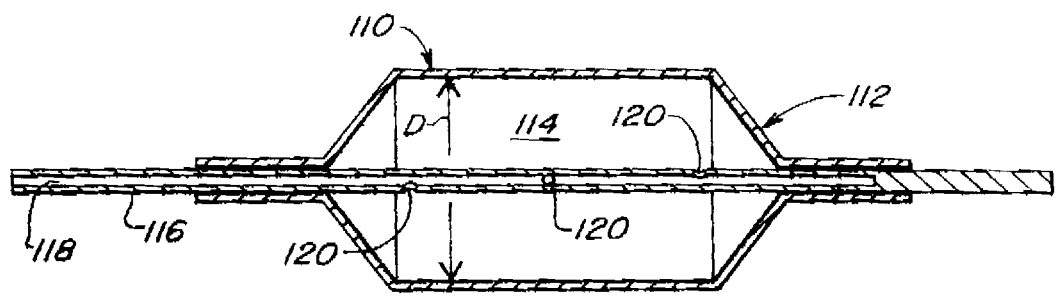
FIG. 4B is a side elevational view in cross-section of the inelastic balloon and the expanded fluoropolymer tube of FIG. 4A, illustrating the inelastic balloon in an inflated condition in accordance with a method of manufacturing a radially expandable device according to the teachings of the present invention.

Referring specifically to FIG. 4B, the balloon 112 can be inflated by introduction of a pressurized fluid to the lumen 114 of the ePTFE tube 110. The overlying ePTFE tube 110 expands with the inelastic balloon 122 until both the balloon 112 and the ePTFE tube 110 obtain the predetermined size and shape of the inflated balloon 112, step 222 of FIG. 6A. The inflated balloon 112 thus imparts its predetermined size and shape to the ePTFE tube 110. This radially expansion process is referred to as blow-molding. The PTFE tube 110 shown in FIG. 4B is radially expanded from the initial diameter d (FIG. 4A) to an increased diameter D. This radial expansion process may take place in an air, water, or steam-heated chamber that is heated to a temperature between 35° C. and 60° C., preferably 50° C. The elevated temperature can contribute to uniform expansion, both circumferentially and longitudinally, of the ePTFE balloon, as well as uniform wall thickness.

Figure 6A:
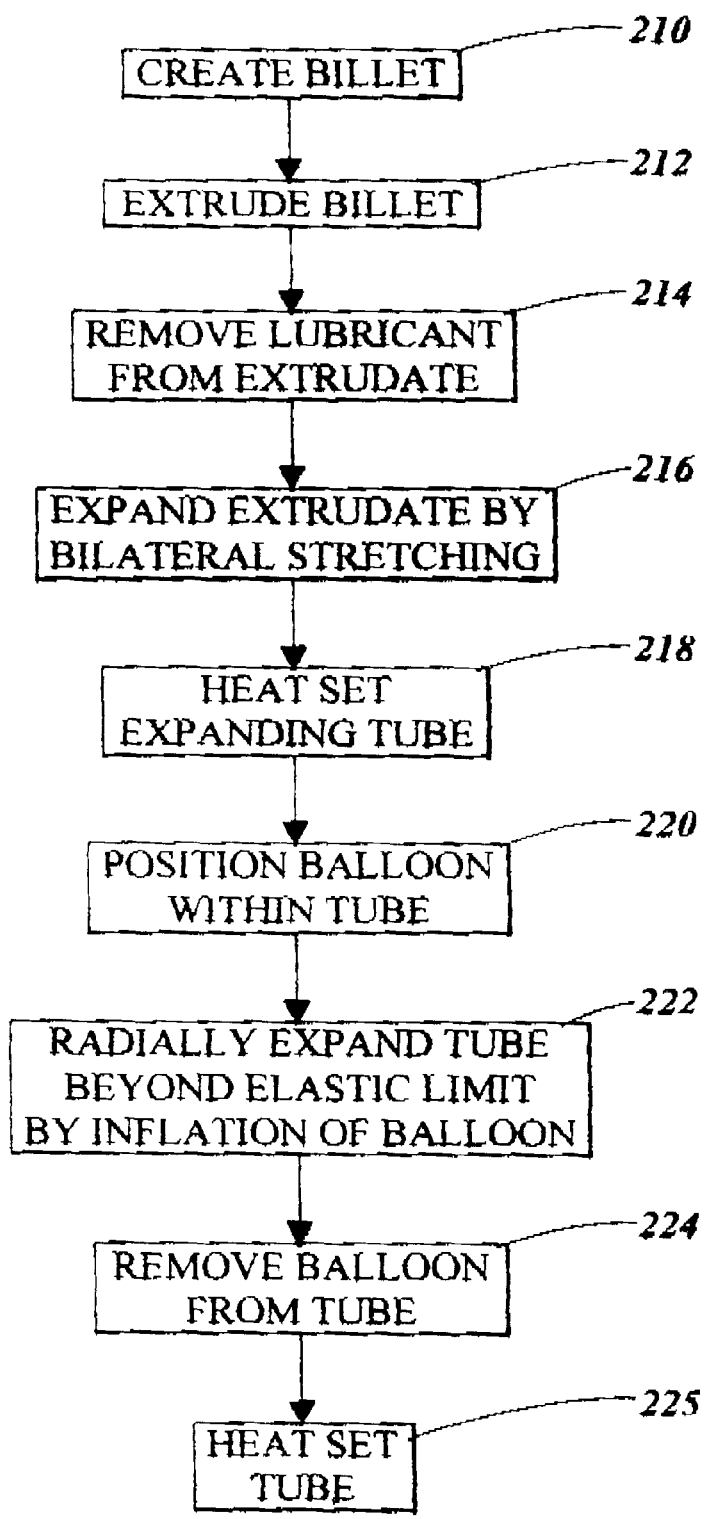
FIG. 6A is a flow chart illustrating the steps of manufacturing a radially expandable device according to the teachings of the present invention.

It is preferable for the ePTFE tube 110 to be plastically deformed by the radial expansion of the inelastic balloon 112, step 222 of FIG. 6A. The terms "plastic deformation" and "plastically deform," as used herein, is intended to include the radial expansion of the ePTFE tube 110 beyond the elastic limit of the ePTFE material such that the ePTFE material is permanently deformed. Once plastically deformed, the ePTFE material forming the tube 110 becomes substantially inelastic, i.e., the ePTFE tube generally will not, on its own, return to its pre-expansion size and shape.

Figure 4C:
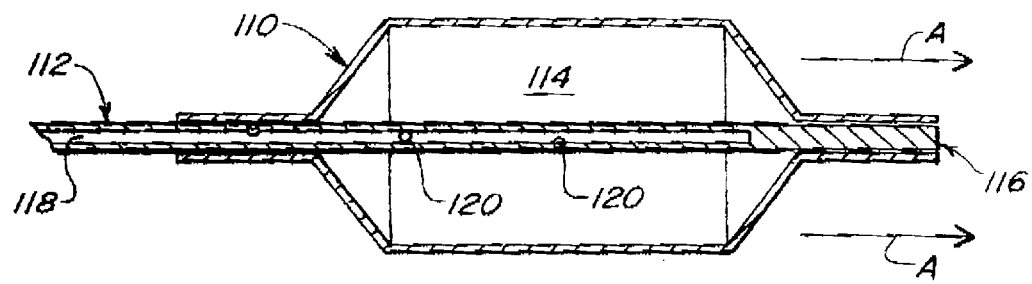
FIG. 4C is a side elevational view in cross-section of the inelastic balloon and the expanded fluoropolymer tube of FIG. 4A, illustrating the removal of the deflated inelastic balloon from the expanded fluoropolymer tube in accordance with a method of manufacturing a radially expandable device according to the teachings of the present invention.

The ePTFE tube 110 can be removed from the balloon 112 by sliding the ePTFE tube 110 relative to balloon 112 and catheter 116, i.e. in the direction of arrows A in FIG. 4C, step 224 of FIG. 6A. The tube 110 can be heat set at a temperature above the sinter point of the material forming the tube, 360° C. for ePTFE, to lock in the structure of the tube 110, step 225 of FIG. 6A.

The resultant radially expanded ePTFE tube 110, produced in accordance with the above described method, provides a radially expandable device, such as expandable device 10 illustrated in FIGS. 1 and 2 and described above, that is radially expandable from a relaxed, collapsed diameter to the second, increased diameter D upon application of a radial deployment force from a deployment mechanism, e.g., hollow tube 20, within the tube 110. The ePTFE tube 110 further provides an expansion device 10 having monolithic construction, that is, a singular, unitary construction of generally homogenous material, ePTFE, that lacks seams or other internal interfaces. The ePTFE tube 110 can be dependably and predictably expanded to the second diameter D upon the application of the radially deployment force within the tube. In particular, the plastically deformed, monolithic microstructure of the ePTFE tube 110, once radially expanded by the inelastic balloon 120, will readily return to the increased diameter D upon application of a radial deployment force and generally will not expand beyond the increased diameter D. The increased diameter D is effectively the maximum expansion diameter for the ePTFE tube, as the increased diameter D is generally independent of the radial deployment force applied to the tube.

Figure 5:
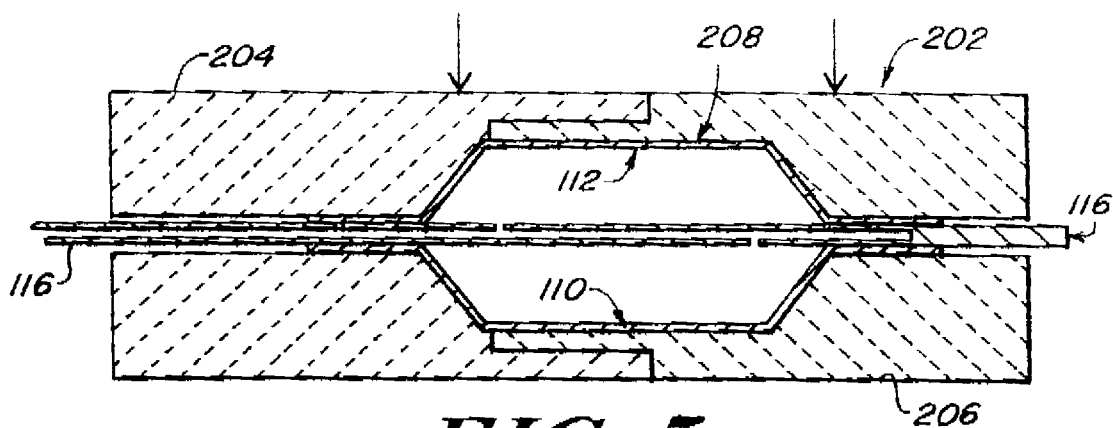
FIG. 5 is a side elevational view of an inelastic balloon and an expanded fluoropolymer tube positioned within the internal cavity of a mold fixture, illustrating the inelastic balloon in a inflated condition in accordance with a method of manufacturing a radially expandable device according to the teachings of the present invention.

Referring to FIG. 5, an alternative method of manufacturing a radially expandable device employing a mold 202 is illustrated. The mold 202 includes two interconnected sections 204 and 206 forming an internal mold cavity 208 for receiving the ePTFE tube 110 with the balloon 112 positioned therein. The mold 202 is preferably constructed of a rigid, unyielding material such as a metal or metal alloy. Suitable metals or metal alloys include brass and steel alloys. The internal mold cavity 208 preferably has a size and shape analogous to that of the inflated balloon 112 to ensure that the inflated balloon 112, and the overlying ePTFE tube 110 concentrically expand.

Figure 6B:
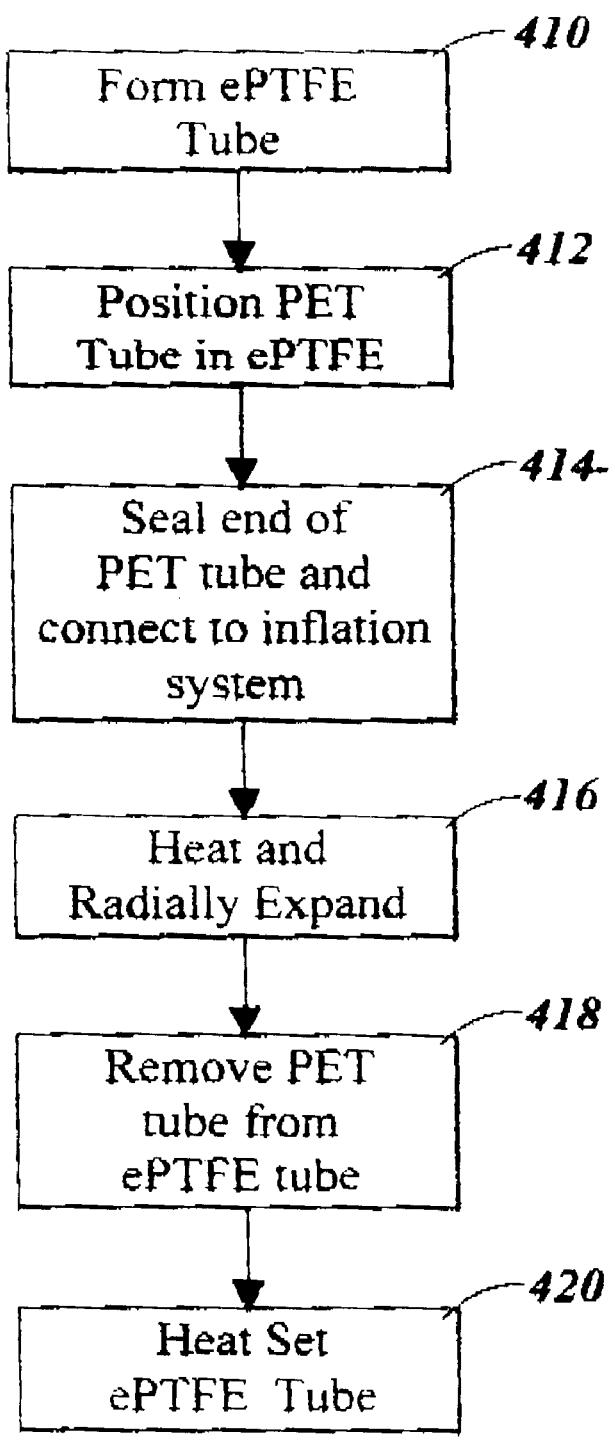
FIG. 6B is a flow chart illustrating the steps of an alternative method of manufacturing a radially expandable device according to the teachings of the present invention.

Referring to the flow chart illustrated in FIG. 6B, a further alternative method of manufacturing a radially expandable device according to the teachings of the present invention will be described. A tube constructed of ePTFE is formed in accordance with the methods described above, step 410. A tube formed of an extruded inelastic material such as PET is used in place of balloon 112 to radially expand the ePTFE tube. The extruded tube is positioned within the ePTFE tube 110, step 412. The extruded tube is then sealed at one end and attached to an inflation system at the other end, step 414.

The extruded tube can then be inflated by an inflation medium to radially expand the ePTFE tube, step 416. The extruded tube and ePTFE tube are preferably heated to the glass transition temperature of the extruded tube, approximately 80° C.–100° C. for PET, as the extruded tube is inflated within the ePTFE tube. It is preferable to limit the temperature of the extruded tube to a temperature less than or equal to the glass transition temperature of the material forming the extruded tube to facilitate removal of the extruded tube from the ePTFE tube. Heating the extruded tube to a temperature above the glass transition temperature will cause the extruded tube to heat set in an expanded configuration, which makes removing the extruded tube from the ePTFE tube difficult. A suitable inflation system employing a hot water chamber for heating the tubes is described in Applicants copending U.S. patent application Ser. No. 09/411,797, filed on Oct. 1, 1999, which is incorporated herein by reference.

After the extruded tube and ePTFE tube are expanded to desired size and shape, the extruded tube is deflated and removed from the ePTFE tube, step 418. The ePTFE tube is then heat set to lock in the structure of the ePTFE tube, step 420.

A mold, such as mold 202, can be employed during radial expansion of the ePTFE tube using the PET tube. The mold is preferably heated within the hot water chamber of the inflation system or by other means such as a hot oil bath or through a steam, hot air, electric, radio frequency or infra red heat source. The mold can be constructed of a material having good heat transfer characteristics, such as metal or metal alloy, for example brass. The mold includes a mold cavity having a size and shape analogous to the desired size and shape of the radially expandable device 10 in the second diameter configuration.

Expansion devices of a wide variety of sizes and shapes may be constructed by altering the geometry of the inelastic balloon 112 or the mold 202. Accordingly, an ePTFE expansion device having a size and shape tailored to a particular function can be manufactured in accordance with the manufacturing methods of the present invention by selecting an inelastic balloon having the desired size and shape. Exemplary expandable fluoropolymer medical treatment devices of different size and shapes are illustrated in FIGS. 7A–7C.

Figure 7A:
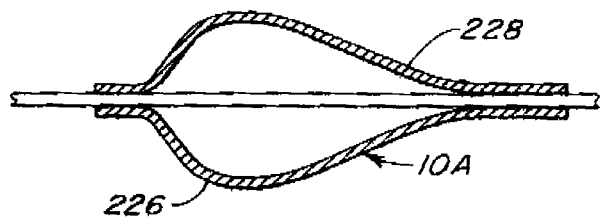
FIG. 7A is a side elevational view in cross section of a generally pear-shaped radially expandable device in accordance with the teaching of the present invention.

FIG. 7A illustrates a radially expandable treatment device 10A having a generally pear-shaped configuration when inflated. The pear shaped configuration is particularly suited for removal of obstructions, such as thrombi and emboli, from a body passage. The expandable treatment device 10A has an increased diameter section 226 that tapers to a reduced diameter section 228. The diameter of the increased diameter section 226 is preferably equal to or slightly less than the diameter of the body passage. The increased diameter section 226 is the primary mechanism for removing obstructions from the body passage and, thus, preferably substantially fills the entire diameter of the body passage to facilitate complete removal of all obstructions from the body passage. The pear-shaped configuration provides the expandable treatment device 10A with a limited, reduced surface area, the increased diameter section 226, which can engage the walls of the body passage and thus minimizes potential damage to the walls of the body passage.

Figure 7B:
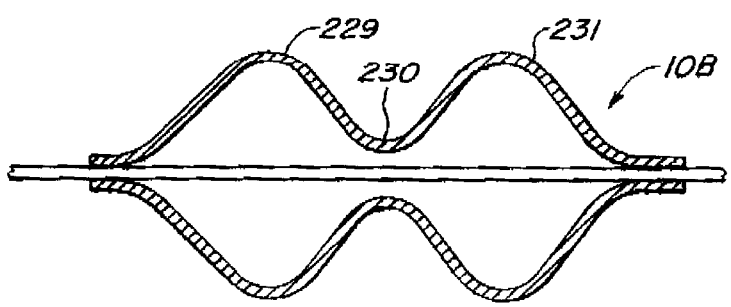
FIG. 7B is a side elevational view in cross section of a generally hour glass shaped radially expandable device in accordance with the teaching of the present invention.
Figure 7C:
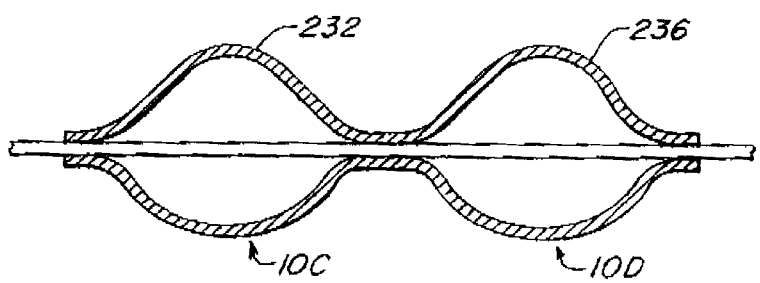
FIG. 7C is a side elevational view in cross section of two coaxially aligned, adjacent radially expandable devices in accordance with the teaching of the present invention.

FIGS. 7B and 7C illustrate alternative exemplary embodiments of the expandable device of the present invention, each providing the device with a reduced surface area for contacting the walls of a body passage. In particular, FIG. 7B illustrates a substantially hour-glass shaped expandable treatment device 10B including, when inflated, a first increased diameter section 229 that tapers to a reduced diameter section 230 that expands to a second increased diameter section 231. As in the case of the exemplary embodiment described above and illustrated in FIG. 7A, the first and second increased diameter sections 229 and 231 preferably have a diameter equal to or slightly less than the diameter of a body passage to be treated to facilitate complete removal of obstructions from the body passage.

FIG. 7C illustrates a third exemplary embodiment in which two axially aligned expandable devices 10C and 10D are provided. As is the case of the second exemplary embodiment described above, the dual expandable devices 10C and 10D together provide a substantially hour-glass configuration that provides the devices with two increased diameter sections 232 and 236.

One feature of the manufacturing processes of the present invention is that the properties of the ePTFE tube 110 forming the expandable device 10 can be manipulated, by varying the extrusion and expansion process parameters, to produce a radially expandable device 10 having different expansion characteristics. For example, the longitudinal stretch ratio of the ePTFE tube 110, i.e., the ratio of final stretched length of the tube to the initial length, and the diametric stretch ratio of the ePTFE tube 110, i.e., the ratio of the final diameter, after longitudinal stretching, and the initial diameter, and the stretch rate can be varied to yield an expansion device having different radial expansion properties. Applicants determined that larger longitudinal stretch ratios, in the order of 2:1 to 3:1, can result in a ePTFE tube having a microstructure characterized by increased internodal distances and interstitial space. Suitable longitudinal stretch ratios can be from 1.1:1 to 10:1. As discussed above, Applicants determined that increased stretch rates yield an ePTFE tube having a fine nodal structure conducive to radial expansion. Expansion devices constructed from ePTFE tubes having such larger longitudinal and/or diametric stretch ratios and which are stretched at increased rates generally require less radial deployment force to expand from the collapsed, reduced diameter configuration to the expanded, increased diameter configuration. Thus, the magnitude of the radial deployment force necessary to expand the ePTFE tube 110 can be pre-selected and manipulated by varying the stretch ratios and stretch rate of the ePTFE tube 110 during the manufacturing process.

In addition to the longitudinal and diametric stretch ratios and the stretch rate, further process parameters can be varied to produce an ePTFE tube 110 having different characteristics. For example, the ePTFE tube 110 can be manufactured to have a porosity that allows for the fluid utilized to radially deploy the ePTFE tube to the expanded configuration to permeate through the walls of the ePTFE tube at a desired flow rate. The process for producing such a microporous ePTFE tube is described in detail in Applicants' copending U.S. patent application Ser. No. 09/411,797, filed on Oct. 1, 1999, which is incorporated herein by reference.

Figure 8:
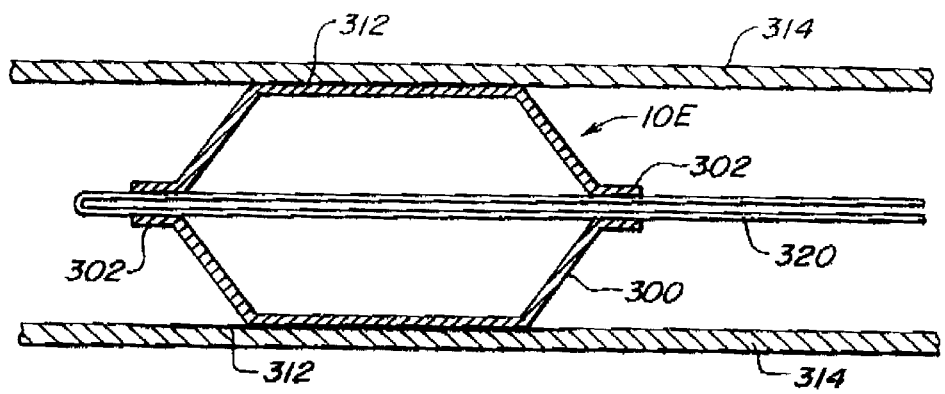
FIG. 8 is a side elevational view in cross section of a catheter deployed dilation balloon according to the teaching of the present invention, illustrating the dilation balloon expanded within a body vessel.

FIG. 8 illustrates an exemplary embodiment of the expandable device of the present invention in which the expandable device 10E is utilized as a catheter deployed dilation balloon 300 for the treatment of a blood vessel 310 partially occluded by plaque deposits 312 adhered to the walls 314 of the blood vessel. The dilation balloon 300 can be manufactured in accordance with the methods of the present invention and is shown in the expanded configuration. The ends 302 of the dilation balloon 300 are bonded to a catheter tube 320, which is used to provide an inflation fluid to the balloon 300 to effect expansion of the balloon 300 to a predefined and fixed maximum diameter.

It will thus be seen that the invention efficiently attains the objects made apparent from the preceding description. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and desired to be secured by Letters Patent is:

1. A method of manufacturing a radially expandable device having a shaped body, the method comprising the steps of:
   forming a tube of expanded fluoropolymer material having an initial diameter and microporous through-pores, the tube having an inlet;
   applying a radial expansion force to the tube through the inlet to expand the tube from the initial diameter to a second diameter and to alter the geometry of the microporous through-pores to thereby form the shaped body, the shaped body having a fine nodal structure conducive to radial expansion by a radial deployment force; and
   removing the expansion force,
   wherein the shaped body is radially expandable from a reduced diameter configuration to the second diameter upon application of the radial deployment force from a deployment mechanism within the shaped body as fluid permeates through the microporous through-pores.

2. The method of claim 1, wherein the deployment mechanism is a fluid.

3. The method of claim 1, wherein the step of radially expanding the plastically deforms the tube beyond its elastic limit.

4. The method of claim 1, further comprising
   heat setting the shaped body after the step of applying a radial expansion force to the shaped tube.

5. The method of claim 1, wherein the second diameter to which the shaped body expands is a maximum diameter.

6. The method of claim 5, wherein the maximum diameter is independent of the radial deployment force applied by the deployment mechanism.

7. The method of claim 1, wherein the step of applying a radial expansion force includes
   inserting a tube of extruded material into the tube, and
   expanding the tube to apply the radial expansion force to the tube.

8. The method of claim 7, wherein the tube and tube are heated to the glass transition temperature of the extruded material during the step of radial expanding.

9. The method of claim 7, further comprising
   providing a mold having an internal cavity,
   positioning the tube and the tube within the internal cavity, and
   radially expanding the tube within the internal cavity.

10. The method of claim 9, further comprising
    heating the tube and the tube to the glass transition temperature of the extruded material during the step of radially expanding the tube within the internal cavity of the mold.

11. The method of claim 1, wherein the step of forming the tube comprises the steps of:
    creating a billet by blending a mixture of a fluoropolymer and a lubricant and compressing the mixture,
    extruding the billet to form an extruded article having a longitudinal axis,
    removing the lubricant from the extruded article,
    expanding the extruded article to form a tube of expanded fluoropolymer material, and
    heat setting the tube.

12. The method of claim 11, wherein the fluoropolymer is polytetrafluoroethylene (PTFE).

13. The method of claim 11, wherein the step of expanding the extruded article further comprises
    bilaterally stretching the extruded article in two opposing directions along the longitudinal axis to yield an article which is substantially uniformly stretched over a major portion of its length and has a microstructure of nodes interconnected by fibrils.

14. The method of claim 13 wherein the step of expanding the extruded article includes
    longitudinally stretching the extruded article from an initial length to a stretched length at a stretch rate.

15. The method of claim 14, further comprising
    selecting an amount of radial deployment force sufficient to radially expand the shaped body to the second diameter by varying a stretch ratio of the stretched length to the initial length.

16. The method of claim 15, further comprising selecting an amount of radial deployment force sufficient to radially expand the shaped body to the second diameter by varying the stretch rate.

17. The method of claim 1, wherein the step of applying a radial expansion force includes
    inserting a balloon into the tube, and
    expanding the balloon to apply the radial expansion force to the tube.

18. The method of claim 17, wherein the balloon and the tube are heated to approximately 35° C.–60° C. during the step of radial expanding.

19. The method of claim 17, wherein the balloon is expanded by inflation with a fluid.

20. The method of claim 19, wherein the balloon is constructed of an inelastic material.

21. The method of claim 20, wherein the balloon is expandable to a predefined size and shape.

22. The method of claim 21, wherein the balloon expands the tube to the predefined size and shape.

23. The method of claim 22, further comprising
    providing a mold having an internal cavity,
    positioning the tube within the internal cavity, and
    radially expanding the balloon within the tube while the tube remains positioned in the internal cavity.

24. The method of claim 23, wherein the internal cavity has a size and shape analogous to the predefined size and shape of the balloon.

25. A method of manufacturing a radially expandable device having a shaped body, the method comprising the steps of:
    forming a monolithic tube of expanded fluoropolymer material having a microporous structure having spaces between microfibrils that define microporous through-pores extending from an inner wall to an outer wall of the tube,
    applying a radial expansion force to the tube to expand the tube from a collapsed diameter to an inflated diameter and to alter the geometry of the microporous through-pores to thereby form the shaped body, the shaped body having a fine nodal structure conducive to radial expansion by a radially applied fluid force; and removing the expansion force, wherein the shaped body is radially and inelastically expandable from the collapsed diameter to the inflated diameter upon application of the radially applied fluid force from a deployment mechanism within the shaped body as fluid permeates through the microporous through-pores.

26. A method of manufacturing a fluid permeatable device having a shaped body, the method comprising the steps of:

forming a monolithic, expanded tube of extruded fluoropolymer material, and further expanding the tube by radially expanding the tube from an initial diameter to a maximum diameter to thereby form the shaped body, the shaped body having uniform through-pores between the microfibril lengths within a wall of the fluoropolymer material and a fine nodal structure conducive to radial expansion by a fluid force, wherein the fluid force can maximize the shaped body to the maximum diameter simultaneous with fluid permeating through the through-pores of the wall between the microfibril lengths and out of the wall, and wherein the maximum diameter and the shape of the shaped body is independent of the fluid force used to maximize the shaped body to the maximum diameter as fluid permeates through the through-pores of the wall of the fluoropolymer material.

* * * * *

UNITED STATES PATENT AND TRADEMARK OFFICE
CERTIFICATE OF CORRECTION

PATENT NO. : 6,395,208 B1
DATED : May 28, 2002
INVENTOR(S) : Herweck et al.

It is certified that error appears in the above-identified patent and that said Letters Patent is hereby corrected as shown below:

Column 1,
Line 42, replace "constructed a fluoropolymer" with -- constructed of a fluoropolymer --;

Column 6,
Line 56, replace "process of the forming the tube" with -- process of forming the tube --;

Signed and Sealed this

Twenty-fourth Day of February, 2004

JON W. DUDAS
*Acting Director of the United States Patent and Trademark Office*